United States Patent [19]

Abere

[11] Patent Number: 5,695,339
[45] Date of Patent: Dec. 9, 1997

[54] METHOD AND APPARATUS FOR REATTACHING A DETACHED CROWN OF AN INSTALLED DENTAL BRIDGE

[76] Inventor: Dennis J. Abere, 623 Crestwood Dr., Waukesha, Wis. 53188

[21] Appl. No.: 439,688

[22] Filed: May 12, 1995

[51] Int. Cl.$^6$ .................. A61C 5/08; A61C 5/04
[52] U.S. Cl. .................. 433/218; 433/219; 433/90
[58] Field of Search .................. 433/89, 90, 218, 433/219, 226, 215; 604/275, 278, 239, 270

[56] References Cited

U.S. PATENT DOCUMENTS

| | | | |
|---|---|---|---|
| 881,469 | 3/1908 | Hale | 604/239 |
| 1,125,887 | 1/1915 | Schimmel | 604/239 |
| 2,696,670 | 12/1954 | Thurman | 433/90 X |
| 3,421,222 | 1/1969 | Newman | 433/226 X |
| 3,487,544 | 1/1970 | Weissman | 433/218 |
| 3,788,321 | 1/1974 | Reither et al. | |
| 3,854,209 | 12/1974 | Franklin et al. | 433/90 |
| 4,172,323 | 10/1979 | Orlowski | |
| 4,255,140 | 3/1981 | Marshall | 433/90 X |
| 4,391,391 | 7/1983 | Robaldo | |
| 4,402,671 | 9/1983 | Westerman | 433/218 |
| 4,431,414 | 2/1984 | Lawrence | 433/90 |
| 4,689,013 | 8/1987 | Lustig | |
| 4,728,321 | 3/1988 | Chen | |
| 4,740,160 | 4/1988 | Hruska | |
| 4,863,428 | 9/1989 | Chevalier | 604/239 |
| 4,973,248 | 11/1990 | Sigler | |
| 5,183,397 | 2/1993 | Weissman | 433/218 X |
| 5,236,361 | 8/1993 | Mays | |
| 5,324,199 | 6/1994 | Branemark | |

FOREIGN PATENT DOCUMENTS

| | | |
|---|---|---|
| 608662 | 12/1993 | Germany |
| 931181 | 6/1982 | U.S.S.R. |
| 1456126 | 4/1985 | U.S.S.R. |
| 1358951 | 11/1985 | U.S.S.R. |

Primary Examiner—Nicholas D. Lucchesi
Attorney, Agent, or Firm—Gerald R. Harmon; John A. Beehner

[57] ABSTRACT

A method for reattaching to a first abutment tooth a detached crown of a dental bridge having at least one other crown fixed onto a second abutment tooth includes the steps of forming a vent hole through the detached crown, inserting the open tip of a syringe needle into the vent hole, preliminarily securing and sealing the needle in the vent hole and thereafter applying a flowable dental adhesive material such as an acrylic resin to securely reinforce the connection between the needle and crown and seal any gap therebetween. The void under the detached crown is then washed by ejecting fluids through the needle with a syringe barrel. A flowable dental cement is then ejected through the needle to fill the void between the crown and abutment tooth. Upon curing of the cement, the acrylic resin is dislodged from the surface of the crown enabling withdrawal of the needle from the vent hole which is then plugged.

The syringe apparatus of the invention includes a barrel and plunger coupled to a needle having exterior surface irregularities or prongs adjacent but spaced from the open tip of the needle so that they will be covered by the acrylic resin for securing the needle to the crown.

22 Claims, 4 Drawing Sheets

METHOD AND APPARATUS FOR REATTACHING A DETACHED CROWN OF AN INSTALLED DENTAL BRIDGE

BACKGROUND OF THE INVENTION

1. Technical Field

The present invention is directed generally to a method and apparatus for reattaching to a first abutment tooth a detached crown of a dental bridge having at least one other crown fixed onto a second abutment tooth. More specifically, the method of the invention includes steps for rigidly securing and effectively sealing a syringe needle within a vent hole through the detached crown to enable flowable materials to be ejected onto the first abutment tooth under pressure without said flowable materials dislodging said needle or escaping between any gap between the needle and vent hold. Likewise, the apparatus of the invention is more specifically directed to such a syringe needle having exterior surface irregularities adjacent to but spaced from the open tip of the needle for coacting with cured flowable dental adhesive materials on said detached crown to reinforce said needle against both rotational and axial movement.

2. Description of the Prior Art

For many years, a technique has been employed in the dental profession for replacing a missing tooth or teeth with a fixed bridge. A pontic tooth is typically used to replace the patient's missing teeth. In the case of two or more missing teeth, two or more pontic teeth can be fixed together. In addition to a pontic tooth or tooth, the fixed bridge will consist of two or more dental crown. In case of a single missing tooth, one crown will be affixed to one side of the pontic tooth and the other crown to the opposite side of the pontic tooth. In the case of two or more pontic teeth connected together in line, one crown will be attached to the pontic tooth on one end of the line and the other crown to the pontic tooth on the opposite end of the line. The more common method used by the dental profession for securing this type of bridge is cementing the crowns to the patient's natural teeth immediately adjacent to the patient's missing natural tooth or teeth. To facilitate alignment and height of the bridge with the patient's other natural teeth, enamel is removed from the top and side surfaces of each of the two natural abutment teeth. While there are other methods of securing such a fixed bridge device to the abutment teeth, the most common method employs only a cement or adhesive to secure the bridge in place on the two abutment natural teeth.

It is not uncommon for a fixed dental bridge cemented to natural abutment teeth to have one or both crowns detach from its abutment natural tooth thereafter. In the situation where both crowns have become detached and the bridge is no longer fixed and can be removed from the mouth, it may be feasible to resecure the original bridge using a process similar to that employed for the initial securing of the device in the patient's mouth. In cases where only one of the two crowns has detached from an abutment tooth, it may be advantageous and feasible to forcibly detach the second crown from the other abutment tooth. Again, the original bridge may be resecured using a process similar to that used to secure it initially in the patient's mouth, assuming that the original dental bridge has not been damaged.

In situations where only one of the two crowns has become detached and the other end of the bridge device is still firmly fixed to its abutment tooth, the dentist has several concerns. Included among those is the concern that efforts to forcibly remove the attached crown to permit removal of the bridge device will result either in damage to the bridge or harm to either the abutment tooth or the other surrounding dental tissues.

The problems noted in attempting to forcibly remove an attached crown once the other crown has become detached are not intended to be exhaustive. Other problems and considerations may also arise. In the absence of detaching both crowns of the fixed bridge from their respective abutment tooth, there is a severe limitation on the ability to apply a second application of glue or adhesive to the ground top and side surfaces of the one abutment tooth from which the crown has become detached. Accordingly, there is a real and significant need in the art for an improved method particularly designed for applying a further application of cement or adhesive to the top and sides of a natural abutment tooth for the detached crown of a fixed bridge wherein the other crown of the bridge remains attached throughout.

It has previously been known to drill a vent hole through approximately the center of a detached bridge crown and inject a flowable dental cement through the vent hole for reattaching the crown, but the known method has certain shortcomings which limits its effectiveness. The intended tight press fit of a needle into a vent hole through a crown necessarily results in gaps being formed between the needle and vent hole through which at least very flowable fluids can pass. Thus, the ability to disinfect, wash and dry the abutment tooth is compromised since fluids injected for those purposes can escape through the gap around the needle without accomplishing the intended function.

Accordingly, a primary object of the invention is to provide an effective method and apparatus for reattaching to a first abutment tooth, a detached crown of a dental bridge, having at least one other crown fixed onto a second abutment tooth.

Another object is to provide such a method wherein a needle injected through a vent hole in a detached crown is rigidly but detachably adhered to the crown, with any gap between the needle and vent hole effectively sealed to prevent back flow of fluids therethrough.

Another object is to provide such a method which guards against flow of adhesive material between the needle and vent hole which could result in plugging of the open tip of the needle.

Another object is to provide such a method wherein the inserted needle is effectively reinforced against both rotational and axial movements.

Another object of the invention is to provide such a method which is simple to follow, effective in operation and cost saving for patient's on whom the method is practiced.

SUMMARY OF THE INVENTION

The method for reattaching to a first abutment tooth a detached crown of a dental bridge having at least one other crown fixed onto a second abutment tooth includes the steps of forming a small vent hole through the detached crown to expose a portion of the first abutment tooth. A syringe needle of a size to substantially fill the vent hole is then inserted therein, preferably to a depth short of protruding through the detached crown. The needle is then preliminarily secured within the vent hole and any gap between the needle and vent hole is at least partially sealed to guard against adhesive flow through that gap during reinforcement of the needle. The needle is reinforced by applying an adhesive material onto the detached crown around the needle to secure the needle relative to the detached crown and effectively seal any gap between the needle and vent hole. Thereafter, disinfectant, antibacterial, rinse water and air may be injected through the needle in that order to disinfect, rinse and dry the first abutment tooth with assurance that such fluid effectively washes over the surface of the abutment tooth since any escape route through the gap between the needle and vent hole is sealed. Thereafter, a flowable dental cement is inserted into a syringe barrel which is coupled to the needle for injection onto the first abutment tooth.

Pressure is preferably applied to urge the crown against the abutment tooth as the dental cement cures. Thereafter, excess cement is flaked off the border of the crown by the gum line. The flowable dental adhesive material is dislodged from the outer surface of the crown and the needle is then withdrawn from the vent hole which is then plugged with amalgam, a resin plug or the like. The injected cement not only adheres the previously detached crown onto the abutment tooth, but it also seals any space therebetween to keep fluids therefrom which would otherwise result in dental disease.

The apparatus of the invention for reattaching a detached crown of a dental bridge to an abutment tooth includes a syringe having a barrel for containing flowable materials and a generally tubular needle having an open tip for dispensing flowable material therefrom. The barrel is coupled to the needle for fluid flow therebetween and a plunger or the like is operative to force flowable material in the barrel through the needle for expelling it from the open tip. The needle has exterior surface irregularities at a position adjacent to but spaced from the open tip so that, upon insertion of the open tip into the vent hole of a detached crown and upon creating a buildup of flowable dental adhesive material on the detached crown around the exterior surface irregularities, said needle is reinforced against both rotational and axial movement and any gap between the needle and vent hole is effectively sealed. The exterior surface irregularities may comprise a plurality of prongs protruding outwardly from the needle.

DESCRIPTION OF THE PREFERRED EMBODIMENT

Figure 1:
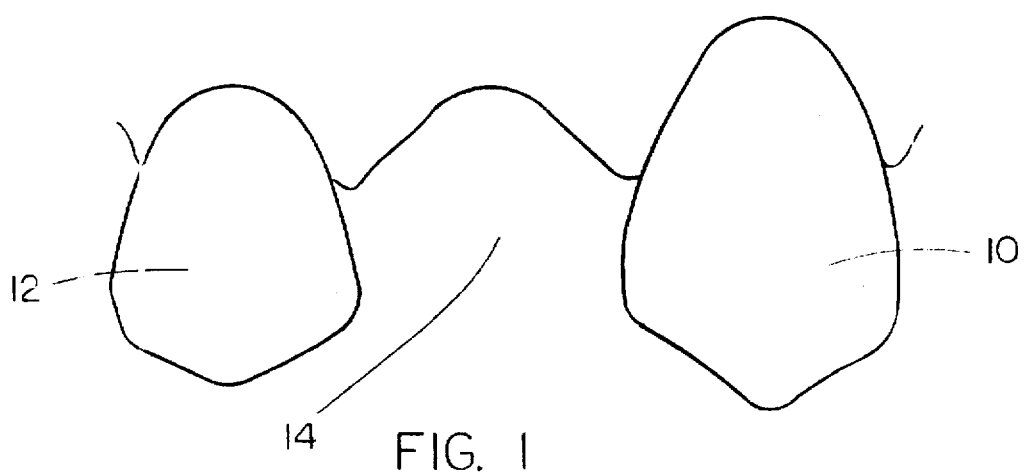
FIG. 1 is a partial side view of two natural teeth having an edentulous area therebetween.
Figure 2:
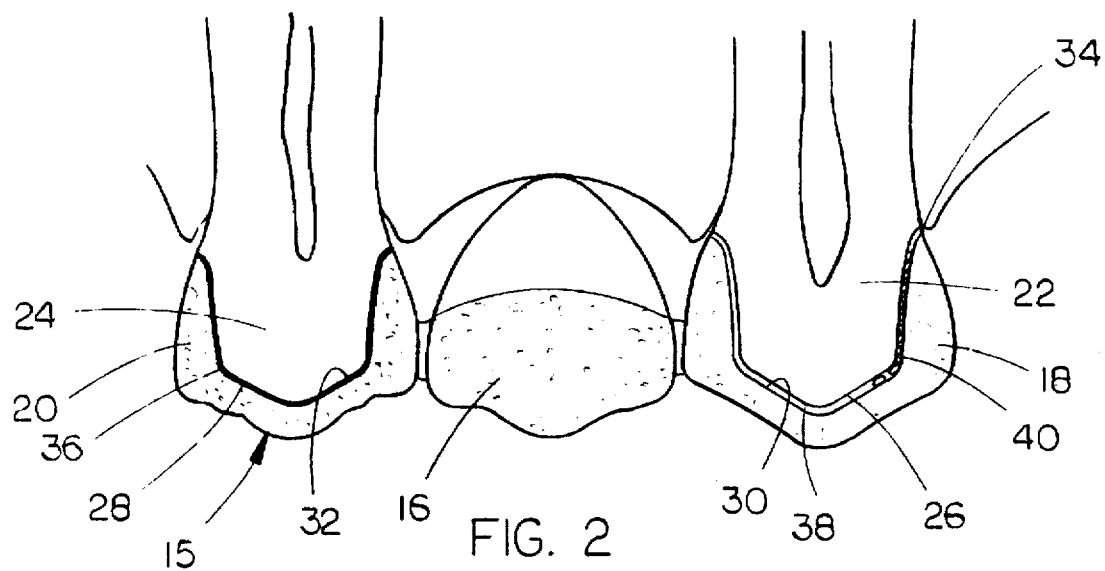
FIG. 2 is a side sectional view showing the natural teeth ground to present first and second abutment teeth, a bridge including a single pontic between a pair of crowns, with one crown detached from its abutment tooth and moisture being drawn into the gap therebetween.
Figure 3:
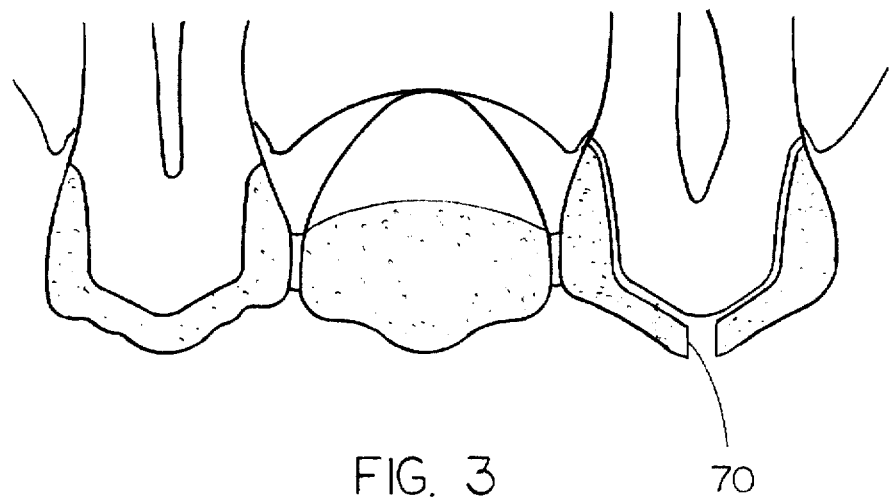
FIG. 3 is a similar sectional view with an abutment hole drilled through the detached crown.

Certain background information is helpful for understanding the need for the present invention and how it resolves that need. FIG. 1 illustrates a portion of a human mouth showing two natural teeth 10 and 12 separated by an edentulous area 14 for a single missing tooth. A dental bridge is generally prepared to provide a permanent replacement tooth or pontic for aesthetic reasons as well as to, prevent migration of the adjacent teeth 10 and 12 into the edentulous area. FIG. 2 illustrates the three-tooth bridge that has been prepared for this situation. It includes a single replacement tooth or pontic 16 arranged between and rigidly secured first and second crowns 18 and 20. Whereas a three-unit bridge is disclosed in the drawings, the number of pontic teeth and bridges and the arrangement of pontic teeth and bridges relative to one another is not material to the present invention.

As is conventional, first and second teeth 10 and 12 have had the enamel thereon ground down to present first and second abutment teeth 22 and 24, each presenting a respective prepared surface 26 and 28.

The first crown 18 of the bridge 15 has an inside surface 30 having a contour approximately matching the contour of the prepared surface 26 of the first abutment tooth 22. The second crown 20 has an inside surface 32 having a contour approximately matching the contour of the prepared surface 28 of the second abutment tooth 24. The exterior and interior surfaces of each crown meet to form the crown margin 34. On the second abutment tooth 24, dental cement 36 seals and fills the area between the inside surface 32 of the second crown 20 and the prepared surface 28 of the second abutment tooth 24, depicting a fully attached second crown 20. On the first abutment tooth 22, a void 38 is depicted between the inside surface 30 of the first crown 18 and the prepared surface 26 of the first abutment tooth 22, depicting a detached first crown 18. Within the void 38 surrounding the prepared surface of the first abutment 22 is shown fluid 40, which has peculated into the void 38. The fluid 40 would be expected to contain saliva, bacteria, food and other organics which, if allowed to remain, would contribute to tooth decay. The fluid is peculated into the void 38 through a slight, almost imperceptible, movement of the end of the bridge 15 having the detached crown 18, moving first away from the first abutment tooth 22 and then towards it.

Figure 4:
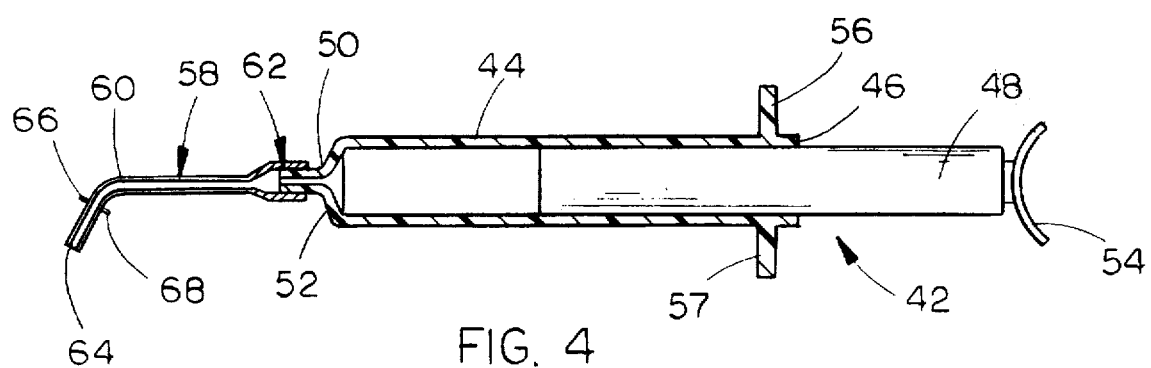
FIG. 4 is a side sectional view of a syringe apparatus of the present invention.
Figure 5:
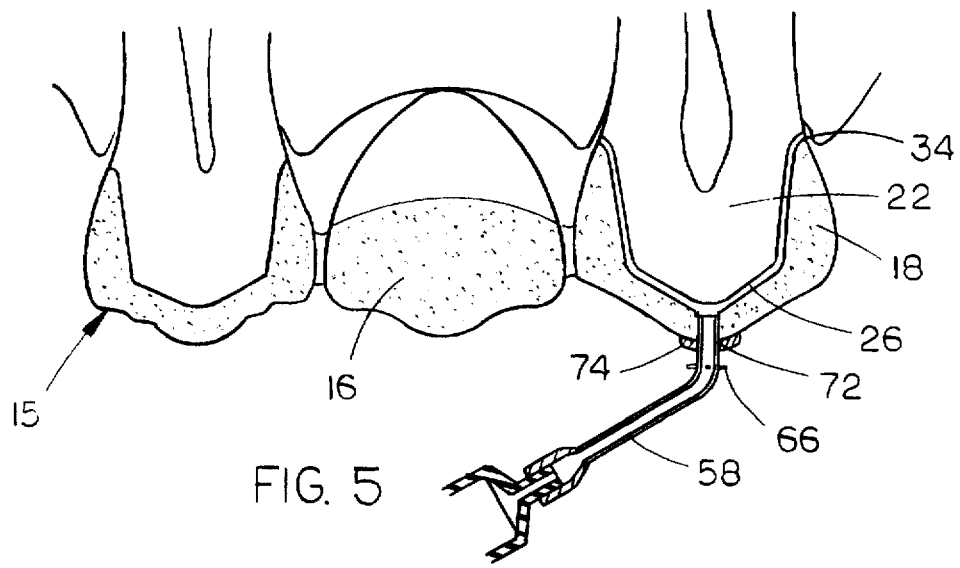
FIG. 5 is a similar cross-sectional view showing the syringe needle inserted into the vent hole and preliminarily retained therein by a light-cured resin.
Figure 6:
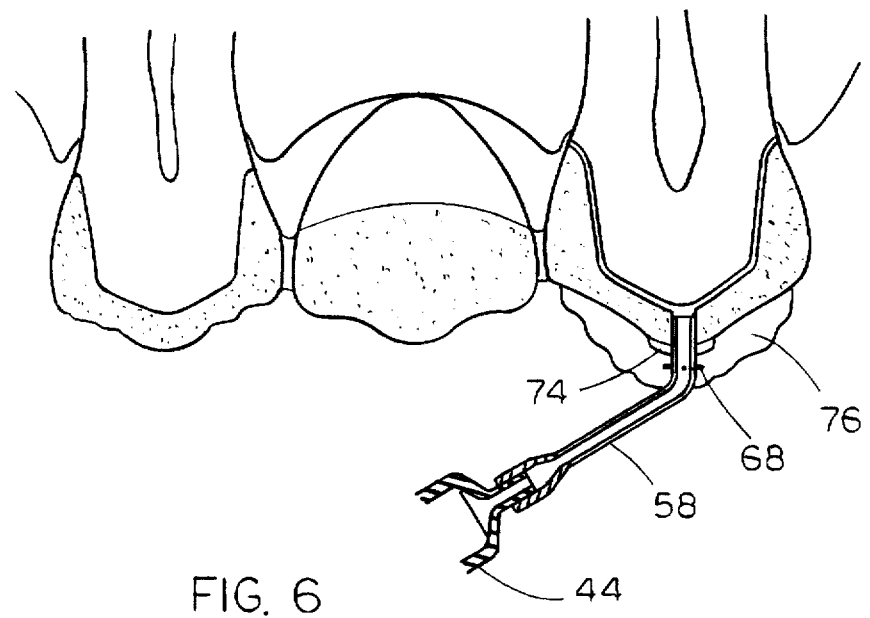
FIG. 6 is a similar cross-sectional view showing the needle rigidly fixed and sealed on the detached crown with a buildup of acrylic grout resin on the detached crown.
Figure 7:
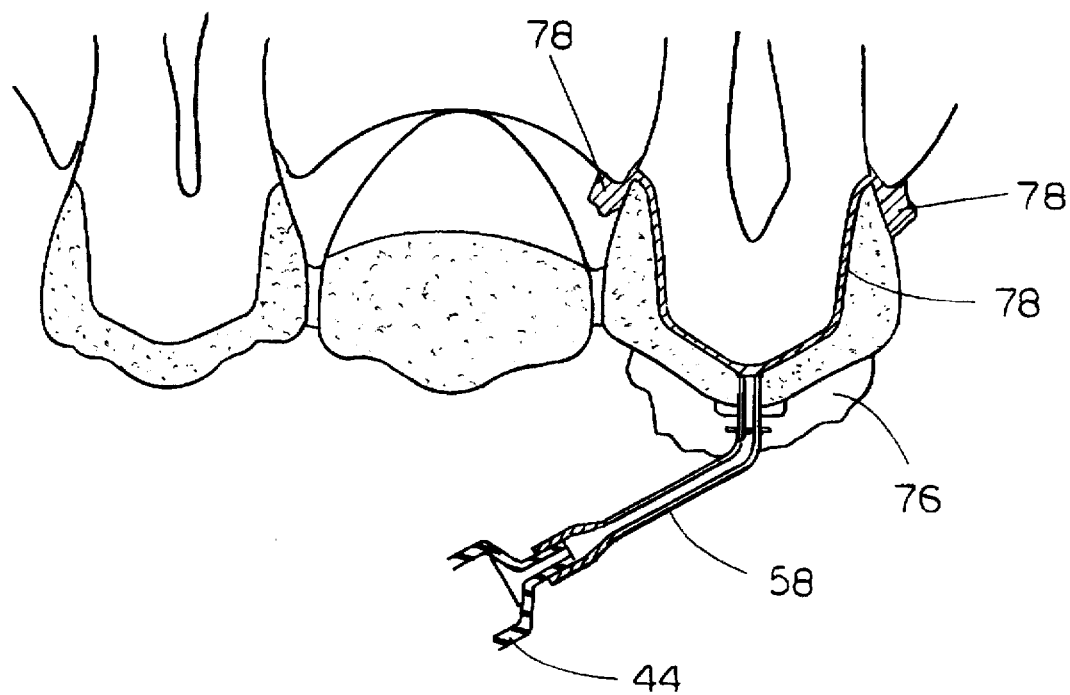
FIG. 7 is a similar cross-sectional view showing the gap between the abutment tooth and crown filled with dental cement and surplus cement around the bridge at the gum line.
Figure 8:
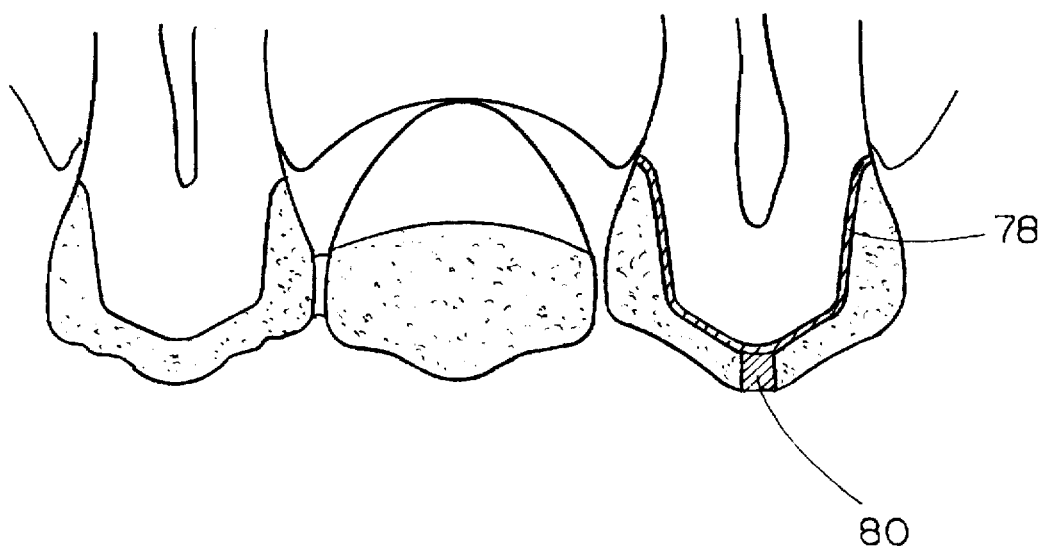
FIG. 8 is a similar cross-sectional view showing the reattached crown with surplus cement removed and the vent hole plugged.
Figure 9:
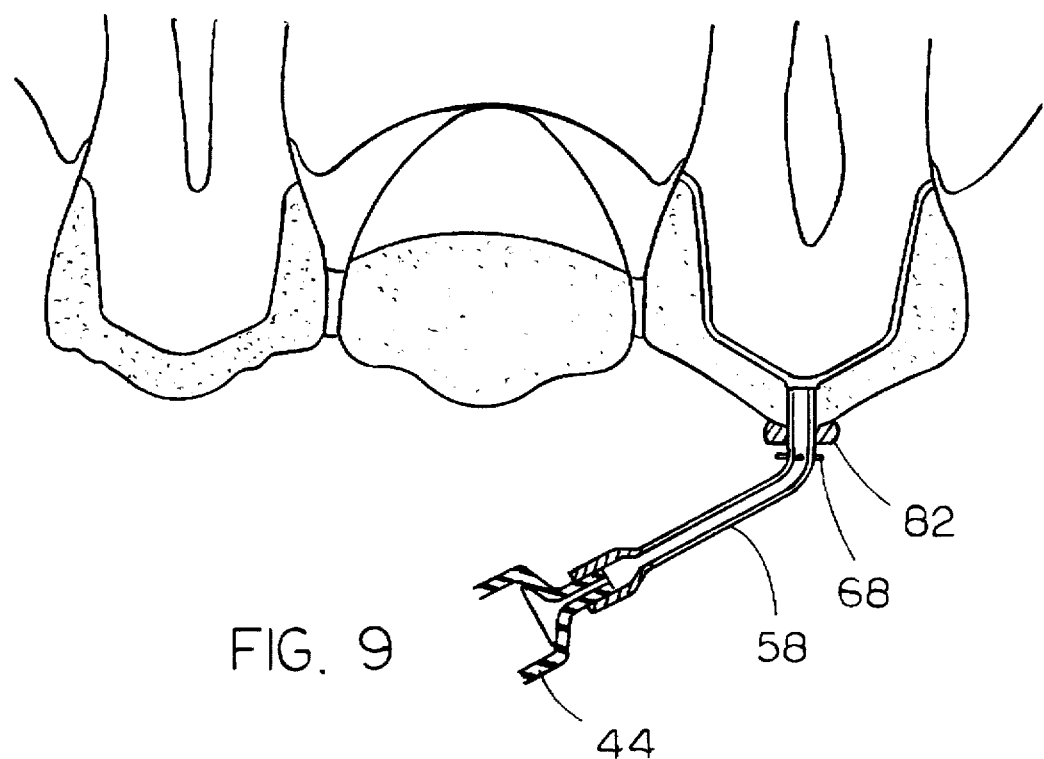
FIG. 9 is a similar cross-sectional view showing the needle preliminarily secured to the crown by a light curable resin impregnated bushing.
Figure 10:
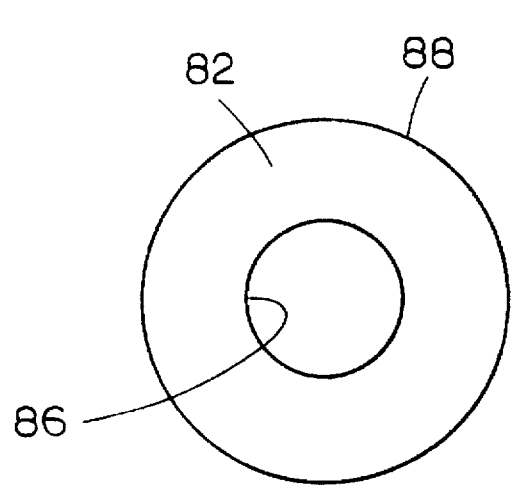
FIG. 10 is a top plan view of the bushing.
Figure 11:
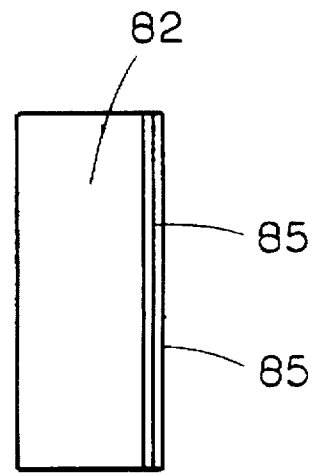
FIG. 11 is a side view of the bushing.

Generally the preferred procedure for reattaching a single detached crown is to remove the entire bridge since this enables the dentist to check the abutment teeth, clean the inside surface of the crowns and reattach the bridge as in the original installation procedure. The fixed crown 20 might be removed by popping it off the second abutment tooth 24 by banging it off with a percussion hammer. Alternatively, a very sticky and chewy "dental candy" is sometime effective for dislodging the attached crown. Problems associated with such removal, however, include damage to the abutment tooth and possible fracture of the porcelain or ceramic material of the bridge. In the past, if one crown could not be removed, the attached crown would be cut nearly in half and pride apart to break the glue bond. Damage to the bridge may require that it be replaced with a new bridge, which is an expensive solution for either the patient or dentist. In some cases, the bridge just can't be removed and the dentist may feel the limit of reasonable force has been applied. The method of the present invention provides a procedure for reattaching such a bridge wherein one or more but less than all of the crowns of bridge had become detached. It is preferred that the syringe apparatus shown in FIG. 4 be used for this procedure.

To reattach a fixed bridge on which less than all of the crowns can be removed from their respective abutment teeth without significant risk of damage to the bridge or to the abutment teeth, the following general technique can be followed. Initially, a syringe is selected having a barrel for containing dental cement suitable for resealing the void under the detached crown and having a needle allowing the expression of the cement from the barrel of the syringe and through the needle. The needle should have a generally flat tip from which the cement or other such materials may be expelled from the syringe.

Following selection of a suitable syringe, a vent hole should be formed by removing a portion of the detached crown entirely between the exterior surface and the interior surface. The vent hole should be located in an area where it will have the minimal adverse impact upon the appearance of the bridge to a casual viewing of the patient's mouth and teeth and as near to the point which is of greatest distance from the gum along all sides of the crown. The size of the vent hole should be such to permit the tip of the syringe needle to penetrate into the vent hole through to the inside surface of the crown. Syringe 42 includes a barrel 44 for containing flowable materials. The rearward end 46 is open for receiving a plunger 48 that is moveable into the barrel to force fluid therein out through a reduced diameter threaded neck 50 at the forward end 52 of barrel 44. Plunger 48 has a saddle rest 54 on its rearward end which is used in cooperation with opposite finger grips 56 and 57 on the barrel to advance the plunger 48 into the barrel.

A generally tubular needle 58 includes a bent shaft 60 having a flared internally threaded rear coupling portion 62 adapted to have the barrel neck 50 screwed into it. The opposite end of the needle is preferably a blunt open tip 64 for ejecting fluids therefrom.

The needle 58 has external surface irregularities 66 which, in the illustrated embodiment are prongs 68. The surface irregularities or prongs 68 are positioned adjacent to but spaced from the open tip 64 for a purpose described below.

Additionally, the needle 58 has a circular bushing 82 of a pliable or moldable material, such as fiber, saturated or impregnated with a light curable resin material positioned on the needle between the tip 64 and the prongs 68. It may be either fixed to the needle tip or merely movably positioned. Applied to the flat surface of the bushing closest to the tip of the needle is a coating of pressure sensitive adhesive 84 and a removable backing sheet 85 for sticking/attaching the bushing to the contour of the crown around the edge of the vent hole 70. The bushing has a circular opening 86 in its center having a diameter approximately equal to the diameter of the needle 58. The outer edge 88 of bushing 82 should extend optimally 2-3 millimeters from the needle. The adhesive coating to the pliable bushing permits the bushing to be easily molded to the contour of the exterior surface of the crown around the vent hole 70 and held in place until the light curable resin has been cured through application of the appropriate light to the resin material.

Reattachment of a bridge may be facilitated if the dentist has several barrels available for use with a single syringe needle 58.

With the syringe 42 available, the first step of the method according to the present invention is to drill a vent hole 70 through the detached crown 18 to expose a portion of the first abutment tooth 22. The vent hole 70 has a size and shape to be substantially filled by the needle 58. The open tip 64 of needle 58 is inserted into the vent hole 70 to an extent such that the open tip 64 should stop short of protruding through the detached crown 18.

The next step is to preliminarily secure the needle 58 within the vent hole 70 and at least partially seal any gap 72 between the needle and vent hole. Because of minute surface irregularities between exterior surface of the needle and interior surface of the vent hole, even a frictional press fit of the needle within the vent hole does not preclude some gap 72 forming around a substantial portion of the needle through which at least gaseous fluid could pass.

One way of preliminarily securing the needle in place is to apply a light-curable resin 74 around the needle at the point of contact with the surface of detached crown 18. The purpose of the preliminary securement step is primarily to sea gap 72 to prevent a later applied flowable dental adhesive material from penetrating the gap and plugging the needle. Secondarily, it positions the needle for application of the flowable dental adhesive material 76 which may be an acrylic resin of the type commercially available under the trademark "Duralay". This type of resin is more adhesive than the light curable resin 74. The acrylic resin 76 is preferably built up around the needle to strengthen the connection between the needle and crown 18 and to increase the pressure capabilities of the seal around the needle.

Once the acrylic resin 76 has cured, the following steps are performed in an effort to remove saliva, bacteria, food and other organics from the void 38 under the crown 18. A barrel 44 containing a disinfectant may be coupled to the needle 58. The plunger 48 is depressed to force the disinfectant to be expelled from the open tip of the needle and to wash over the first abutment tooth 22. Upon detachment of barrel 44, another barrel with an antibacterial, solution may similarly be used to wash the abutment tooth 22. It is preferred that the abutment tooth again be washed by ejecting distilled rinse water from another barrel through needle 58. Finally, an empty barrel may be coupled to the needle for forcing air through void 38 to substantially dry the area.

Next, a barrel of a flowable dental cement 78 is coupled to the needle and the plunger is depressed to eject to the cement 78 into the void until it escapes out from around the base of the crown. Whereas the particular type of dental cement 78 is not critical to the invention, zinc phosphate and a glass ionomer are preferred.

Immediately after the cement 78 has been ejected, the pressure is applied to the bridge 15 to urge previously detached crown 18 toward the abutment tooth 22. Pressure can be applied manually by the dentist or patient, or by the force of the patient's jaw with an insert applied between the upper and lower teeth so that force is not applied to the needle.

As the cement 78 is cured, the excess cement protruding from the crown margin is flaked off with a dental instrument to assure a clean smith edge at the crown margin.

Finally, the acrylic resin 76 is pried off of the previously detached crown 18 with a sharp dental instrument thereby enabling withdrawal of the needle 58 from vent hole 70.

The final step is to plug the top of the vent hole 70 with amalgam or a resin plug 80 or the like.

The exterior surface irregularities or prong 66 on needle 58 are particularly helpful for securing the needle relative to the crown by the acrylic resin buildup 76. That resin covers the prongs thereby affords additional reinforcement against both rotational axial movement of the needle relative to the crown.

An alternative way of preliminarily securing the needle 58 in vent hole 70 is to provide a generally circular bushing of an pliable material such as fiber saturated or impregnated with a light curable resin, sliding the bushing onto the needle 58 with the needle in place and the bushing 82 moved into engagement with the surface of the crown 18, using a dental instrument to tap the bushing into gap 72 and applying an appropriate light source to the light curable resin material 74 so as to cure the resin material and affix the needle in position. Use of the bushing 82 is not critical to the invention, but is an effective alternate way of applying the preliminary sealing resin 74.

Whereas the method and apparatus of the invention have been shown and described in connection with preferred embodiments thereof, it is apparent that many modifications, substitutions and additions may be made which are within the intended broad scope of the appended claims.

I claim:

1. A method for reattaching to a first abutment tooth a detached crown of a dental bridge having at least one other crown fixed onto a second abutment tooth, comprising,
   providing a syringe including a barrel for containing flowable materials including dental resins, a generally tubular needle having an open tip for dispensing flowable material therefrom, coacting detachable coupling means on said needle and barrel for coupling said barrel to said needle for fluid flow therebetween and means for forcefully moving flowable material in said barrel through said needle and expelling said flowable material from said open tip,
   forming a vent hole through the detached crown to expose a portion of the first abutment tooth, said vent hole having a size and shape to be substantially filled by said needle,
   inserting the open tip of the needle into said vent hole,
   preliminarily securing said needle within said vent hole and at least partially sealing any gap between said needle and vent hole,
   applying a flowable dental adhesive material onto said detached crown around said needle to secure said needle relative to said detached crown and effectively seal any gap between the needle and vent hole,
   providing a flowable dental cement in said barrel,
   operating the syringe to expel the flowable dental cement through the open tip of the needle and onto the first abutment tooth,
   allowing said flowable dental cement to cure,
   dislodging said flowable dental adhesive material from said detached crown,
   removing the needle from the vent hole, and
   filling said vent hole.

2. The method of claim 1 wherein the step of inserting said needle into said vent hole includes stopping said needle at a position short of protruding from the underside of said detached crown.

3. The method of claim 1 wherein the step of preliminarily securing said needle and at least partially sealing any gap between the needle and vent hole is operative to block flow of said flowable dental adhesive material through said gap and past said open tip of the needle.

4. The method of claim 1 wherein said step of preliminary securing said needle comprises applying a preliminary dental adhesive material to the gap between said needle and vent hole.

5. The method of claim 4 wherein said preliminary dental adhesive material is a light-curable resin.

6. The method of claim 4 wherein said step of applying a preliminary dental adhesive material comprises applying said preliminary dental adhesive material to a generally annular bushing, placing said bushing around said needle, and engaging said bushing against said needle and detached crown.

7. The method of claim 6 wherein said step of engaging said bushing against said detached crown includes urging said bushing into any gap between said needle and vent hole.

8. The method of claim 1 wherein the step of applying a flowable dental adhesive material onto said detached crown comprises creating a buildup of said flowable dental adhesive material on said detached crown around said needle.

9. The method of claim 8 wherein said flowable dental adhesive material comprises an acrylic resin.

10. The method of claim 1 further comprising a disinfectant solution in said barrel and operating said syringe to expel said disinfectant solution over said first abutment tooth prior to expelling said flowable dental cement therethrough.

11. The method of claim 10 further comprising providing rinse water in said barrel and operating said syringe to expel said rinse water onto said first abutment tooth prior to expelling said flowable dental cement therethrough.

12. The method of claim 11 further comprising operating said syringe to expel air over said first abutment tooth for drying it prior to expelling said flowable dental cement from said needle.

13. The method of claim 1 further comprising applying pressure to said detached crown to urge said detached crown toward said first abutment tooth while allowing said flowable dental cement to cure.

14. The method of claim 1 wherein the step of dislodging said flowable dental adhesive material from said detached crown comprises using a sharp dental instrument to pry said cured flowable dental adhesive material from said crown.

15. The method of claim 1 wherein said step of filling said vent hole comprises restoring the configuration of the detached crown approximately to its shape preceding the step forming said vent hole.

16. The method of claim 1 wherein the step of providing said tubular needle comprises providing exterior surface irregularities on said needle at a position adjacent whereby, upon insertion of said needle into said vent hole, said exterior surface irregularities cooperate with said flowable dental adhesive material to secure said needle against both rotational and axial movement relative to said detached crown.

17. The method of claim 16 wherein said exterior surface irregularities comprise a plurality of prongs protruding outwardly from the exterior surface of said needle.

18. An syringe apparatus for reattaching to a first abutment tooth a detached crown of a dental bridge having at least one other crown fixed onto a second abutment tooth, said detached crown having a vent hole therethrough to expose a portion of the first abutment tooth, said syringe apparatus comprising,
   a barrel for containing flowable materials,
   a generally tubular needle having an open tip for dispensing flowable material therefrom,
   means for coupling said barrel to said needle for fluid flow therebetween and means for forcibly moving flowable material in said barrel through said needle and expelling said flowable material from said open tip,
   said needle having exterior surface irregularities at a position adjacent to but spaced from said open tip whereby, upon insertion to said open tip into said vent hole and creating a buildup of flowable dental adhesive material on said detached crown around said exterior surface irregularities, said needle is reinforced against both rotational and axial movement, and a bushing on said needle between said open tip and said surface irregularities, said bushing being impregnated with a light curable adhesive whereby, upon insertion of said needle into said vent hole to the extent that said bushing engages said crown and upon applying a light to cure said light curable resin, said needle is preliminarily secured within said vent hole.

19. The syringe apparatus of claim 18 wherein said bushing is fixed on said needle.

20. The syringe apparatus of claim 18 wherein said bushing is slidably movable on said needle.

21. The syringe apparatus of claim 18 wherein said bushing comprises a ring of absorbent fiber material.

22. The syringe apparatus of claim 18 wherein said bushing has a top surface facing said surface irregularities and a bottom surface facing said open tip, an adhesive layer on said bottom surface and a peel off backing sheet removably engaging said adhesive layer.

* * * * *